US008008480B2

(12) United States Patent
McElroy et al.

(10) Patent No.: US 8,008,480 B2
(45) Date of Patent: Aug. 30, 2011

(54) PROCESS FOR THE PURIFICATION OF MELOXICAM

(75) Inventors: Liam McElroy, Antrim (GB); Lillian Cromie, County Down (GB); Mark Garret, Belfast (GB)

(73) Assignee: Norbrook Laboratories Ltd, Newry (IE)

( * ) Notice: Subject to any disclaimer, the term of this patent is extended or adjusted under 35 U.S.C. 154(b) by 0 days.

(21) Appl. No.: 12/396,044

(22) Filed: Mar. 2, 2009

(65) Prior Publication Data

US 2009/0163707 A1 Jun. 25, 2009

Related U.S. Application Data

(63) Continuation of application No. 11/940,619, filed on Nov. 15, 2007, now abandoned.

(30) Foreign Application Priority Data

Nov. 20, 2006 (GB) .................................. 0623113.8

(51) Int. Cl.
*C07D 279/16* (2006.01)
(52) U.S. Cl. ........................................................ 544/49
(58) Field of Classification Search ..................... 544/49
See application file for complete search history.

(56) References Cited

U.S. PATENT DOCUMENTS 4,233,299 A * 11/1980 Trummlitz et al. ......... 514/226.5
2003/0109701 A1 * 6/2003 Coppi et al. .................... 544/49

* cited by examiner

*Primary Examiner* — Taylor Victor Oh
(74) *Attorney, Agent, or Firm* — Cooley LLP

(57) ABSTRACT

A process for purifying meloxicam form I from a crude meloxicam, which comprises:
i. contacting the crude meloxicam with an amine in a non-aqueous solvent to form a meloxicam salt;
ii. isolating the meloxicam salt;
iii. dissolving the meloxicam salt in an aqueous solvent to form a salt solution; and
iv. adding an acid to the salt solution to precipitate free meloxicam.

15 Claims, No Drawings

PROCESS FOR THE PURIFICATION OF MELOXICAM

CROSS-REFERENCE TO RELATED APPLICATION

This application is a continuation of U.S. patent application Ser. No. 11/940,619, filed on Nov. 15, 2007, now abandoned which claims priority to United Kingdom Patent Application No. GB0623113.8, filed on Nov. 20, 2006, each of which are incorporated by reference in their entireties herein.

BACKGROUND

The present invention relates to a process for the purification of 4-hydroxy-2-methyl-N-(5-methyl-2-thiazolyl)-2H-1,2-benzothiazine-3-carboxamide-1,1-dioxide of the Formula (I):

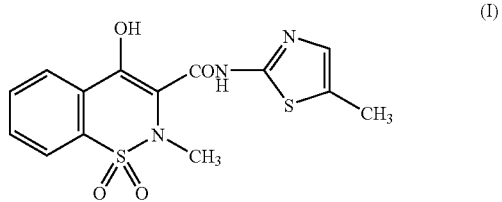

The compound of formula (I) is also known as meloxicam.

Meloxicam is an acid enol class of Non Steriodal Anti-inflammatory (NSAID), first described in EP-A-2482, which inhibits the prostaglandin synthetase/cyclo-oxygenase (COX) class of enzymes, specifically COX (II). This COX (II) specificity makes meloxicam particularly useful for the treatment of chronic inflammatory based diseases such as osteo and rheumatoid arthritis, due to the reduced side effects associated with long term use of other, less specific NSAIDs like aspirin and paracetamol.

These other NSAIDs have the disadvantage of inhibiting COX II and COX I giving rise to peptic ulcers due to their acidic nature irritating the gastric mucosa and their inhibition of prostaglandin synthesis by COX I. Prostaglandins play an important role in protecting the gastrointestinal tract from corrosive gastric enzymes and acids.

Meloxicam can exist in a number of polymorphous forms. The most important pharmaceutical form is form I. Other polymorphic forms II, III and V have been described in US2003/0109701 but these are of little therapeutic relevance. As used herein, meloxicam will exclusively refer to the polymorph form I.

There are a number of known processes to purify the crude meloxicam product which can be prepared according to the process described in EP-A-2482 which reacts a methylic or ethylic ester of 4-hydroxy-2-methyl-2H-1,2-benzothiazine-3-carboxylate-1,1-dioxide with 2-amino-5-methyl-thiazole.

EP-A-2482 describes a method of further purifying this crude meloxicam product by crystallising it out of solvent such as ethylene chloride. However, this purification step is neither commercially useful nor environmentally acceptable.

Other known meloxicam form I purification processes are known as follows:

EP-A-1462451 describes a meloxicam purification process which avoids the use of organic solvents as described in EP-A-2482. This comprises dissolving the crude meloxicam in a mixture of water and NaOH and subsequent addition of an acid to precipitate the crystalline form of meloxicam I, during which a temperature of between 65° C. and the reflux temperature is maintained.

EP-A-1645559 describes a non-aqueous purification process which involves treating crude meloxicam with an alcohol solution of an alkaline alcoholate. This is then acidified and the precipitated meloxicam is then filtered. The filtrate is thereafter crushed in a polar aprotic solvent, and dried after further filtration. This process provides purified meloxicam with less than 0.05% of the impurity 4-hydroxy-2-methyl-N-ethyl-N'-(5-methyl-2-thiazolyl)-2H-1,2-benzothiazine-3-carboxamide-1,1-dioxide.

WO 2006/064298 describes a method of dissolving meloxicam potassium salt in an aqueous solvent, removing insoluble impurities and acidifying the resulting solution and crystallising the meloxicam out. The resulting meloxicam is essentially free of the 4-hydroxy-2-methyl-N-alkyl-(5-methyl-2-thiazolyl)-2H-1,2-benzothiazine-3-carboxamide-1,1-dioxide impurity.

P. Luger et al, European Journal of Pharmaceutical Science, 4, (1996) 175 to 187, describes the formation of basic meloxicam salts and subsequent recrystallisation of meloxicam from water-isopropanol or tetrahydrofuran (THF).

The present invention provides a surprisingly simple two step meloxicam purification process from the crude state, and further provides meloxicam of very high purity.

The most significant impurity in the meloxicam purified according to the current invention and other known processes is the previously mentioned 4-hydroxy-2-methyl-N-alkyl-(5-methyl-2-thiazolyl)-2H-1,2-benzothiazine-3-carboxamide-1,1-dioxide impurity. Advantageously, the process of this invention is able to provide meloxicam with less than 0.05% of this impurity and any other impurity.

Meloxicam purified according to this process satisfies all requirements described within the British Pharmacopia monograph for Meloxicam and also pass the recently proposed draft U.S. monograph.

Additionally this process is advantageous over previous methods in that it removes the 4-hydroxy-2-methyl-N-alkyl-(5-methyl-2-thiazolyl)-2H-1,2-benzothiazine-3-carboxamide-1,1-dioxide impurity and other impurities in both steps of an essentially two step process, hence reducing them to safe levels.

The present invention provides a process for purifying meloxicam form I from a crude meloxicam, which comprises:

i. contacting the crude meloxicam with an amine in a non-aqueous solvent to form a meloxicam amine salt;
ii. isolating the meloxicam salt;
iii. dissolving the meloxicam salt in an aqueous solvent to form a salt solution; and
iv. adding an acid to the salt solution to precipitate free meloxicam.

The crude meloxicam is preferably in solid form, for example in the form of a powder. It may be prepared by any means, for example by the method described in EP-A-2482 in which a methylic or ethylic ester of 4-hydroxy-2-methyl-2H-1,2-benzothiazine-3-carboxylate-1,1-dioxide is reacted with 2-amino-5-methyl-thiazole.

The amine may, for example, be a primary, secondary, tertiary or quaternary amine. N-methylglucamine and triethylamine are generally preferred.

Preferably the non-aqueous solvent is an alcohol, more preferably is one or more of methanol, ethanol, isopropanol and butanol. Most preferably the alcohol is ethanol.

The crude meloxicam is generally dissolved at a temperature above room temperature, for example from 25° C. to 70° C., preferably 50° C. to 70° C., more preferably about 60° C.

Preferably the crude meloxicam is dissolved in the alcohol, especially ethanol, with triethylamine or N-methylglucamine at a temperature of from 25° C. to 70° C., preferably 50° C. to 70° C., most preferably at about 60° C.

Optionally, any remaining undissolved solids are filtered off using standard filtration techniques.

Preferably, the salt, in particular the N-methyglucamine or triethylamine salt, is precipitated out of solution by dropwise addition of an antisolvent. Preferably the antisolvent is an acid alcohol ester, for example an alkyl acetate such as one or more of methyl acetate, ethyl acetate, isopropyl acetate or butyl acetate. Most preferably the acid alcohol ester is ethyl acetate.

Preferably the precipitated salt of meloxicam is filtered and dried. Optionally the drying process can be in vacuo or by freeze or spray drying.

The meloxicam salt is then dissolved in an aqueous solvent. Pure (100%) water may be used, or a mixture of water and a co-solvent. The co-solvent may be any organic solvent, such as an alcohol, for example methanol, ethanol or butanol, or acetone. More preferably the salt is dissolved in the aqueous solvent at a temperature of from 40° C. to 90° C., preferably from 60° C. to 80° C. and most preferably at about 70° C.

Optionally, carbon can then be added to the meloxicam salt dissolved in hot water to remove any further contaminants. Preferably the carbon is in powdered form. The carbon can, for example, be mixed for from 1 minute to 2 hours before being filtered off. Preferably the carbon is mixed for up to 1 hour and most preferably for from 15 to 30 minutes and then filtered off.

In order to precipitate free meloxicam from the filtrate, the filtrate is, either with the carbon treatment or without, acidified with an acid, preferably to a pH of from 2 to 6.5. More preferably, the filtrate pH is reduced to from 4.0 to 5.5, most preferably about 4.6. A suitable acid is acetic, hydrochloric, sulphuric or phosphoric acid. The filtrate is also preferably heated, for example to from 50° C. to 90° C., preferably to from 60° C. to 80° C., and most preferably to about 70° C.

The filtrate may then be filtered and washed, preferably with water, and dried by standard methods such as spray drying, or in vacuo.

Optionally this dried meloxicam form I can be further reslurried, preferably in acetone, methyl ethyl ketone or methyl isobutyl ketone.

The following Example further illustrates the present invention.

EXAMPLE 1

20.4 g of 4-hydroxy-2-methyl-2H-1,2-benzothiazine-3-carboxylate-1,1-dioxide ethyl ester and 8.8 g of 2-amino-5-methylthiazole are refluxed in 300 ml of o-xylene for 24 hr and the reaction by-product, ethanol, is removed by means of a soxhlet extraction device fitted with 4 A molecular sieves.

The crude meloxicam (4-hydroxy-2-methyl-N-(5-methyl-2-thiazolyl)-2H-1,2-benzothiazine-3-carboxamide-1,1-dioxide) is isolated by cooling and filtration in a yield of 24.0 g (95% of theory).

This crude material is then taken up in 200 ml of ethanol along with 13.5 g of N-methylglucamine. After heating to 60° C. for 30 minutes, the undissolved solids are filtered off and 280 ml of ethyl acetate is added to the filtrate over 90 minutes maintaining a temperature of 60° C. throughout.

After cooling to 5° C. for 2 hours, the desired N-methylglucamine salt of meloxicam is obtained by filtration in a yield of 34.7 g (93% of theory) in the form of a bright yellow solid.

This salt is then dried in vacuo and taken up in 450 ml of deionised water. 1.7 g of CN1 carbon is added to the aqueous solution and after agitation is filtered off with celite after heating to 70° C. for 30 minutes.

The resultant filtrate is then acidified with 8.3 g of acetic acid over a period of 15 minutes maintaining a temperature of 70° C. throughout (final pH=4.6).

The precipitate thus formed is isolated by filtration on cooling to ambient temperature and washed with 100 ml water on the filter. 19.3 g (87% of theory) of purified meloxicam is thus obtained in the form of a yellow solid.

What is claimed is:

1. A process for purifying meloxicam form I from a crude meloxicam, which comprises:
    i. contacting the crude meloxicam with an amine in a non-aqueous solvent to form a meloxicam salt;
    ii. precipitating the meloxicam salt;
    iii. isolating the meloxicam salt by filtration;
    iv. dissolving the meloxicam salt in an aqueous solvent to form a salt solution; and
    v. adding an acid to the salt solution to precipitate free meloxicam.

2. The process of claim 1 wherein the crude meloxicam is in the form of a solid.

3. The process of claim 1 wherein the crude meloxicam is contacted with a primary amine.

4. The process of claim 1 wherein the crude meloxicam is contacted with N-methyl glucamine or triethylamine.

5. The process of claim 1 wherein the non-aqueous solvent comprises an alcohol.

6. The process according to claim 5 wherein the alcohol is ethanol.

7. The process of claim 1 wherein the meloxicam salt is precipitated by addition of an antisolvent.

8. The process according to claim 7 wherein the antisolvent is an acid alcohol ester.

9. The process according to claim 8 wherein the acid alcohol ester is an alkyl acetate.

10. The process of claim 1 wherein the aqueous solvent is water.

11. The process of claim 1 wherein the acid is acetic, hydrochloric, sulphuric or phosphoric acid.

12. The process according to claim 11 wherein the acid is acetic acid.

13. The process of claim 1 wherein carbon is also added to the salt solution.

14. The process of claim 1 wherein the precipitated meloxicam is subsequently filtered, washed and dried.

15. The process of claim 1, which provides the precipitated meloxicam with less than 0.05% of 4-hydroxy-2-methyl-N-alkyl-(5-methyl-2-thiazolyl)-2H-1,2-benzothiazine-3-carboxamide-1,1-dioxide.

\* \* \* \* \*